United States Patent
Zhou et al.

(10) Patent No.: US 8,126,539 B2
(45) Date of Patent: Feb. 28, 2012

(54) METHOD AND APPARATUS FOR MONITORING T-WAVE ALTERNANS

(75) Inventors: Xiaohong Zhou, Woodbury, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1173 days.

(21) Appl. No.: 11/871,405

(22) Filed: Oct. 12, 2007

(65) Prior Publication Data

US 2009/0192398 A1 Jul. 30, 2009

(51) Int. Cl.
*A61B 5/0402* (2006.01)

(52) U.S. Cl. ............. 600/517; 600/509; 600/515; 607/9

(58) Field of Classification Search ................... 600/509, 600/516, 517, 508, 515; 607/2, 9
See application file for complete search history.

(56) References Cited

U.S. PATENT DOCUMENTS

| | | | |
|---|---|---|---|
| 5,117,824 A | 6/1992 | Keimel et al. | |
| 5,312,441 A | 5/1994 | Mader et al. | |
| 5,842,997 A * | 12/1998 | Verrier et al. | 600/518 |
| 6,393,316 B1 | 5/2002 | Gillberg et al. | |
| 6,823,213 B1 | 11/2004 | Norris et al. | |
| 6,983,183 B2 | 1/2006 | Thiagarajan et al. | |
| 2002/0138106 A1 | 9/2002 | Christini et al. | |
| 2004/0002743 A1 | 1/2004 | Park et al. | |
| 2004/0098061 A1 | 5/2004 | Armoundas et al. | |
| 2004/0186527 A1 | 9/2004 | Rouw et al. | |
| 2005/0222511 A1* | 10/2005 | Hadley et al. | 600/515 |
| 2006/0116592 A1 | 6/2006 | Zhou et al. | |
| 2006/0116596 A1 | 6/2006 | Zhou et al. | |
| 2007/0123787 A1 | 5/2007 | Kitajima et al. | |

FOREIGN PATENT DOCUMENTS

WO WO2007013911 A 2/2007

OTHER PUBLICATIONS

Paz et al, "Detection of T-Wave Alternans Using an Implantable Cardioverter-Defibrillator", 2006, pp. 791-797.
International Search Report, PCT/US2008/079006, Jan. 14, 2009, 7 Pages.
Nearing, Bd and Verrier RL. "Modified moving average analysis of T-wave alternans to predict ventricular fibrillation with high accuracy" J Appl Physiol Feb. 2002, pp. 541-549, V 92.

* cited by examiner

*Primary Examiner* — Carl H Layno
*Assistant Examiner* — Pamela M Bays
(74) *Attorney, Agent, or Firm* — Michael C. Soldner (57) ABSTRACT

An implantable medical device and associated method assess T-wave alternans by sensing a cardiac electrogram (EGM) signal and selecting a pair of consecutive T-wave signals from the EGM signal. A first amplitude and a second amplitude from each of the consecutive T-wave signals are determined. The differences between the first amplitudes and the second amplitudes of the consecutive T-wave signal pairs are used to compute a T-wave alternans metric.

21 Claims, 8 Drawing Sheets

METHOD AND APPARATUS FOR MONITORING T-WAVE ALTERNANS

TECHNICAL FIELD

The invention relates generally to medical devices and, in particular, to a device and method for monitoring T-wave alternans in a patient.

BACKGROUND

T-wave alternans is beat-to-beat alternation in the morphology, amplitude, and/or polarity of the T-wave, and can be observed on surface electrocardiogram (ECG) recordings. T-wave alternans (TWA) has been recognized in a variety of clinical conditions, including acquired and congenital long QT syndrome and ischemic heart disease associated with ventricular arrhythmias. TWA is considered an independent predictor for cardiac arrhythmias. Experimentally, TWA has been shown to be a precursor of ventricular tachycardia.

In past practice, TWA has been assessed from surface ECG recordings obtained in a clinical setting as an indication of the long-term risk for ventricular arrhythmias. A Fast Fourier Transform (FFT) method is used for frequency domain analysis of T-waves, and a Modified Moving Averaging (MMA) method is used for time domain analysis of T-waves. The low-amplitude changes in the T-wave signal during TWA, which is on the order of microvolts, requires complicated software to assess TWA from a surface ECG recording of typically 128 heart beats or more during exercise or high-rate atrial pacing. Such methods require storing and analyzing more cardiac cycles than are typically available in an implantable cardioverter defibrillator (ICD). TWA assessment using fewer cardiac cycles for practical implementation in ICDs for use in short-term prediction of the onset of arrhythmias is needed.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
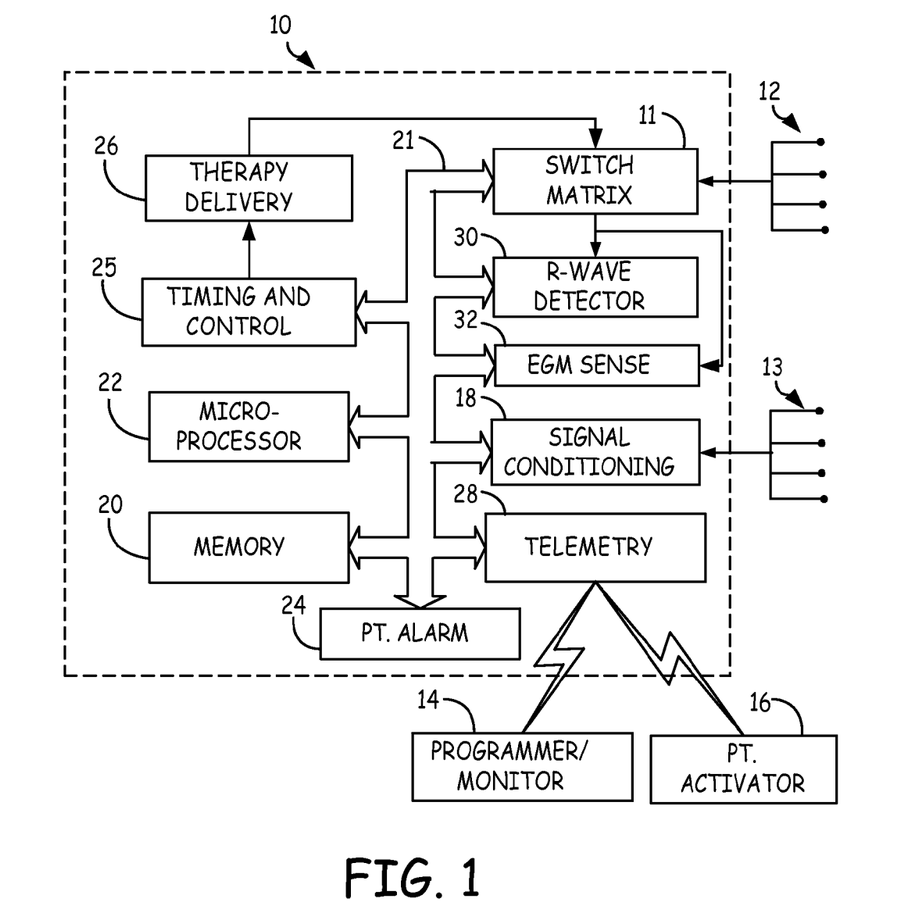
FIG. 1 is a functional block diagram of an IMD system that may be used for monitoring TWA.

FIG. 1 is a functional block diagram of an IMD system that may be used for monitoring TWA. The system provides for dynamic monitoring of TWA in an ambulatory patient. The system includes IMD 10 and associated electrodes 12 for acquiring EGM signals. EGM signals are used by IMD 10 for assessing the cardiac rhythm for determining if and when a therapy is needed. IMD 10 further uses the acquired EGM signals for TWA assessment as will be described herein.

IMD 10 may also be coupled to one or more physiological sensors 13, such as an activity sensor or hemodynamic sensors, such as blood pressure sensors. Physiological signals may be used for detecting cardiac events such as arrhythmias or hemodynamic events. Physiological signals may be used by IMD 10 for triggering certain device operations. In one embodiment, physiological signals are used to trigger a TWA assessment.

IMD 10 is adapted for bidirectional communication with an external programmer/monitor 14 via telemetry circuitry 28. Programmer/monitor 14 is used for programming operating parameters in IMD 10 and for uplinking data from IMD 10. In accordance with one embodiment of the present invention, programmer/monitor 14 may be used by a clinician to initiate a TWA assessment. Alternatively, programmer/monitor 14 may be used to program parameters controlling an automated TWA assessment performed by IMD 10. A TWA report may be received by programmer/monitor 14 from IMD 10 including TWA data and/or TWA assessment results. In some embodiments, EGM data acquired by IMD 10 for use in TWA assessment may be transferred to programmer/monitor 14 for analysis by programmer/monitor 14 or another external computer system such as a remote patient management network. IMD 10 may also be adapted for communicating with a patient activator 16 which may be used by a patient or other caregiver to initiate a TWA assessment.

IMD 10 includes an R-wave detector 30, which receives EGM signals from electrodes 12 via switch matrix 11. R-wave detector 30 includes a sense amplifier having frequency response characteristics and beat-by-beat automatic adjusting sensitivity for accurate R-wave detection. R-wave detection may generally correspond to that disclosed in U.S. Pat. No. 5,117,824 issued to Keimel et al., U.S. Pat. No. 6,393,316 issued to Gilberg et al., or U.S. Pat. No. 5,312,441 issued to Mader, et al., all of which patents are incorporated herein by reference in their entirety.

IMD 10 further includes an EGM sense amplifier 32 that may be used for acquiring EGM signals for specialized signal analyses. EGM sense amplifier 32 receives signals from electrodes 12 via switch matrix 11. EGM sense amplifier 32 provides a wider band of frequency response than R-wave detector 30 and a separately adjustable gain setting. EGM sense amplifier 32 may be embodied as an automatic gain control sense amplifier enabled for automatic gain adjustment responsive to the amplitude of sensed T-wave signals. EGM signal segments for use in specialized analyses, such as TWA assessment, may be extracted from EGM signals obtained by sense amplifier 32 based on relative timing from R-waves detected by R-wave detector 30. In particular, T-wave signal analysis is performed to obtain T-wave measurements during a T-wave sensing window selected relative to an R-wave detection signal from R-wave detector 30.

Electrodes 12 may be located on leads extending from IMD 10 or may be leadless electrodes incorporated in or on the housing of IMD 10. R-wave detector 30 and EGM sense amplifier 32 receive signals from electrodes 12 via switch matrix 11. Switch matrix 11, under the control of microprocessor 22, is used for selecting which electrodes are coupled to R-wave detector 30 for reliable R-wave detection and which electrodes are coupled to EGM sense amplifier 32 for use in TWA assessment.

IMD 10 includes a signal conditioning module 18 for receiving EGM signals from EGM sense amplifier 32 and physiological signals from sensors 13. Signal conditioning module 18 includes sense amplifiers and may include other signal conditioning circuitry such as filters and an analog-to-digital converter. Microprocessor 22 receives signals on system bus 21 from signal conditioning module 18 for detecting physiological events.

Memory 20 is provided for storing conditioned EGM signal output from conditioning module 18. In one embodiment, processing of EGM signals for assessing TWA is performed by IMD microprocessor 22. Microprocessor 22, controls IMD functions according to algorithms and operating parameters stored in memory 20. Microprocessor 22 may perform TWA assessment according to the methods to be described below. In response to TWA assessment results, microprocessor 22 may cause an alert signal to be generated by alarm circuitry 24. Additionally or alternatively, a therapy delivery module 26 may be signaled to deliver or withhold a therapy, or adjust therapy delivery parameters under the control of timing and control circuitry 25. In various embodiments, control circuitry implemented for performing automated TWA assessment in IMD 10 may include application specific integrated circuit (ASIC), an electronic circuit, a processor (shared, dedicated, or group) and memory that execute one or more software or firmware programs, a combinational logic circuit, or other suitable components that provide the described functionality. The implementation of TWA assessment provided herein is not limited to a particular type of system architecture.

In other embodiments, EGM data acquired by IMD 10 for use in TWA assessment may be stored in memory 20 and downlinked to external programmer/monitor 14. All T-wave signal sample points may be stored for use in assessing TWA, or only specified data points may be stored, such as every 30 msec during the T-wave sensing window, for example, if memory space is limited. Processing circuitry included in programmer/monitor 14 may then perform a TWA assessment according to programmed-in algorithms. Reports of TWA assessment results may be generated by either IMD 10 or external programmer/monitor 14, for display, printing or electronic storage such that the results are available for review by a clinician.

Figure 2:
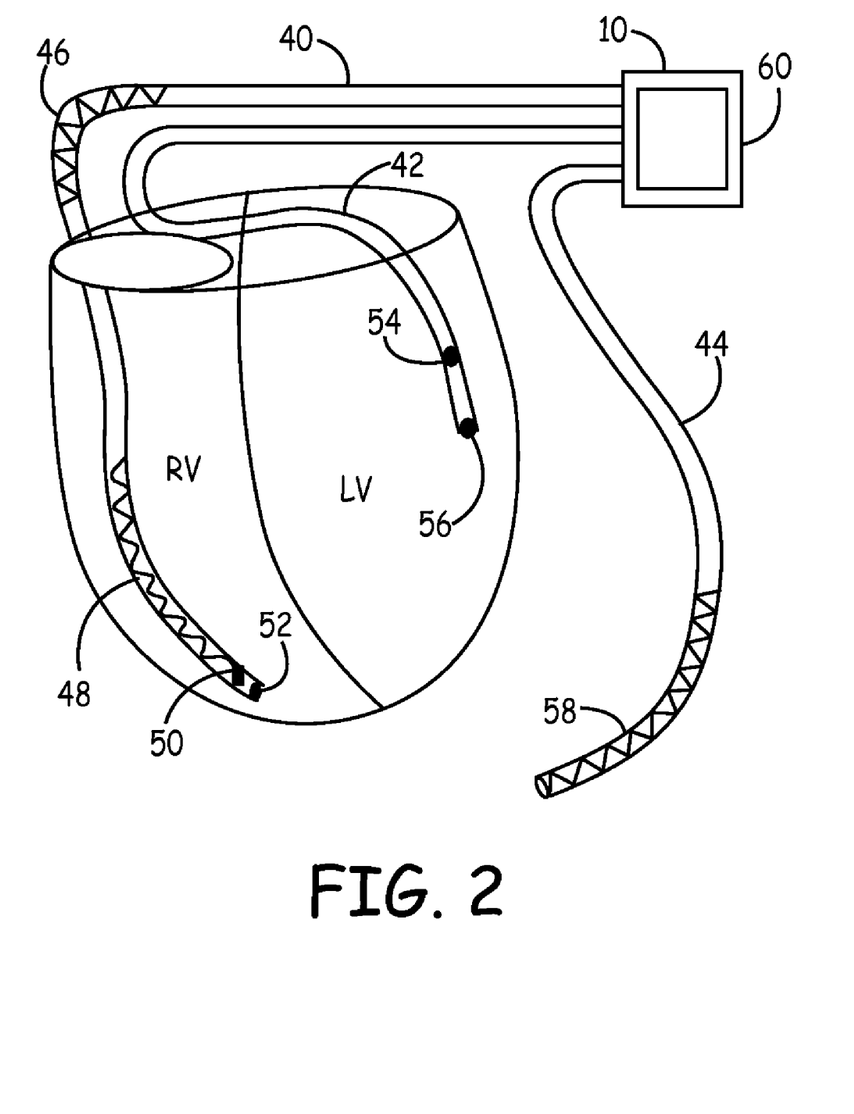
FIG. 2 illustrates one IMD configuration for acquiring EGM data in a TWA assessment method.

FIG. 2 illustrates one IMD configuration for acquiring EGM data in a TWA assessment method. IMD 10 may be embodied as any of a number of IMDs, such as a cardiac monitoring device, a pacemaker, an implantable cardioverter defibrillator, a neurostimulator, or a drug delivery device. EGM data suitable for assessing TWA may be acquired from signals sensed by subcutaneous electrodes, epicardial electrodes, transvenous or endocardial electrodes, or a neurostimulation lead. In one embodiment, multiple sensing vectors are selected for acquiring EGM data for TWA assessment. Multiple sensing vectors may be selected from any combination of available electrodes.

In the example shown in FIG. 2, IMD 10 is embodied as an implantable cardioverter defibrillator and is shown coupled to a set of leads adapted for delivering pacing, cardioversion, and defibrillation pulses and sensing EGM signals for detecting and discriminating heart rhythms. IMD 10 is coupled to a right ventricular (RV) lead 40 carrying a superior vena cava (SVC) coil electrode 46 and an RV coil electrode 48 for use in delivering cardioversion and defibrillation shock pulses. RV lead 40 carries a tip electrode 52 and a ring electrode 50 used in pacing and sensing functions in the right ventricle.

IMD 10 is further coupled to a coronary sinus (CS) lead 42 equipped with a tip electrode 56 and ring electrode 54 for use in sensing and pacing functions in the left heart chambers. CS lead 42 may be advanced into a cardiac vein so as to position CS tip electrode 56 and ring electrode 54 in a desired location over the left ventricle.

IMD 10 is provided with a can or case electrode 60 that may be used in combination with any of the cardiac electrodes for delivering stimulation pulses or sensing cardiac electrical signals in a unipolar mode. IMD 10 may be coupled to one or more subcutaneous leads 44 carrying a subcutaneous electrode 58, which may be a coil, patch or other type of electrode used in combination with SVC coil electrode 46, RV coil electrode 48, and/or can electrode 60 for delivering cardioversion or defibrillation shock pulses. Subcutaneous electrode 58 may alternatively be used in combination with any of the tip or ring electrodes 50, 52, 54 and 56 for sensing or pacing in unipolar modes.

Numerous sensing vectors may be selected from the electrodes available in the system shown in FIG. 2. Any electrode located on RV lead 40 or CS lead 42 may be selected in a unipolar sensing combination with can electrode 60 or subcutaneous electrode 58. Any combination of two electrodes located on RV lead 40 or CS lead 42 may be selected for bipolar sensing. Thus multi-vector sensing for TWA assessment may be achieved by selecting multiple unipolar and/or bipolar sensing electrode pairs, either simultaneously or sequentially, for collecting EGM signals. Both far-field and near-field EGM signals can be collected for TWA assessment. Multi-vector TWA analysis allows discrimination of concordant and discordant forms of TWA. The invention is not limited to the lead and electrode arrangement shown in FIG. 2. Numerous variations exist in the types of leads and electrodes that may be included in a system for monitoring TWA.

Figure 3:
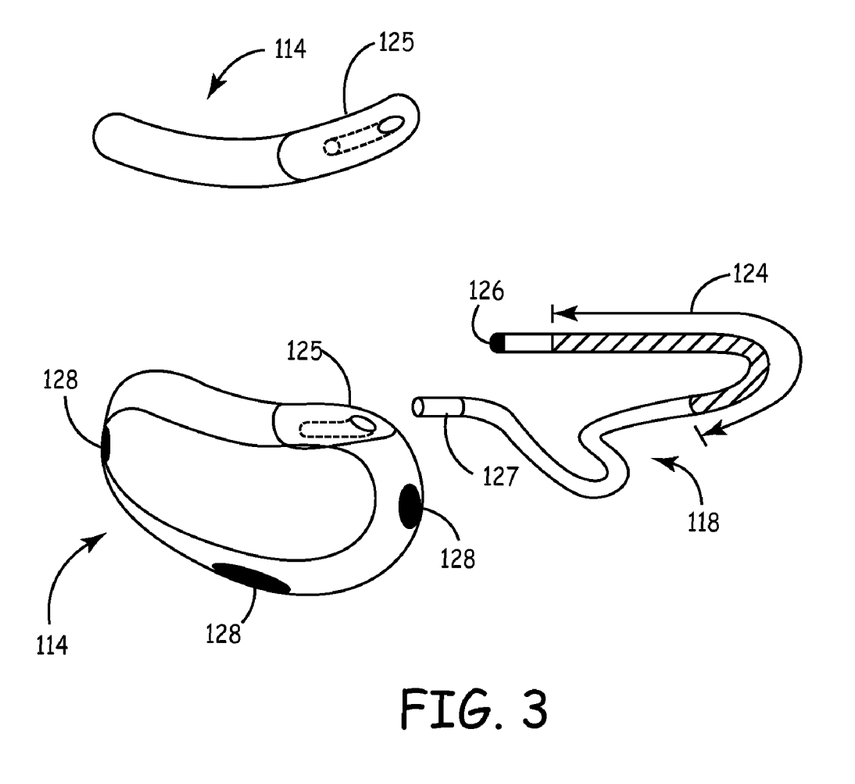
FIG. 3 is a frontal and plan view of a subcutaneous implantable cardioverter defibrillator which may be used for acquiring ECG data in a TWA assessment method.

FIG. 3 is a frontal and plan view of a subcutaneous implantable cardioverter defibrillator (SubQ ICD) 114. The functionality represented by the block diagram of FIG. 1 may be implemented in a device coupled only to subcutaneously implanted electrodes, such as SubQ ICD 114. TWA assessment methods described herein may rely on subcutaneous ECG sensing rather than intracardiac EGM sensing. SubQ ICD 114 includes a housing with a connector 125 for attaching a subcutaneous sensing and cardioversion/defibrillation therapy delivery lead 118.

Subcutaneous lead 118 includes a distal defibrillation coil electrode 124, a distal sensing electrode 126, an insulated flexible lead body and a proximal connector pin 127 for connection to the housing of SubQ ICD 114 via connector 125. SubQ ICD 114 further includes a subcutaneous electrode array (SEA) 128 welded into place on the flattened periphery of the housing of SubQ ICD 114. The SEA 128 is welded to SubQ ICD housing (to preserve hermaticity) and is connected via wires to electronic circuitry inside SubQ ICD 114. The SEA 128 shown in FIG. 3 includes three electrodes positioned to form orthogonal signal vectors. Any of the electrodes included in SEA 128 or on subcutaneous lead 118 may be selected in any combination for sensing subcutaneous ECG signals for use in TWA assessment. The methods described herein for assessing TWA hereinafter refer to the use of EGM signals, however, it is recognized that subcutaneous ECG signals may be substituted for EGM signals.

Figure 4:
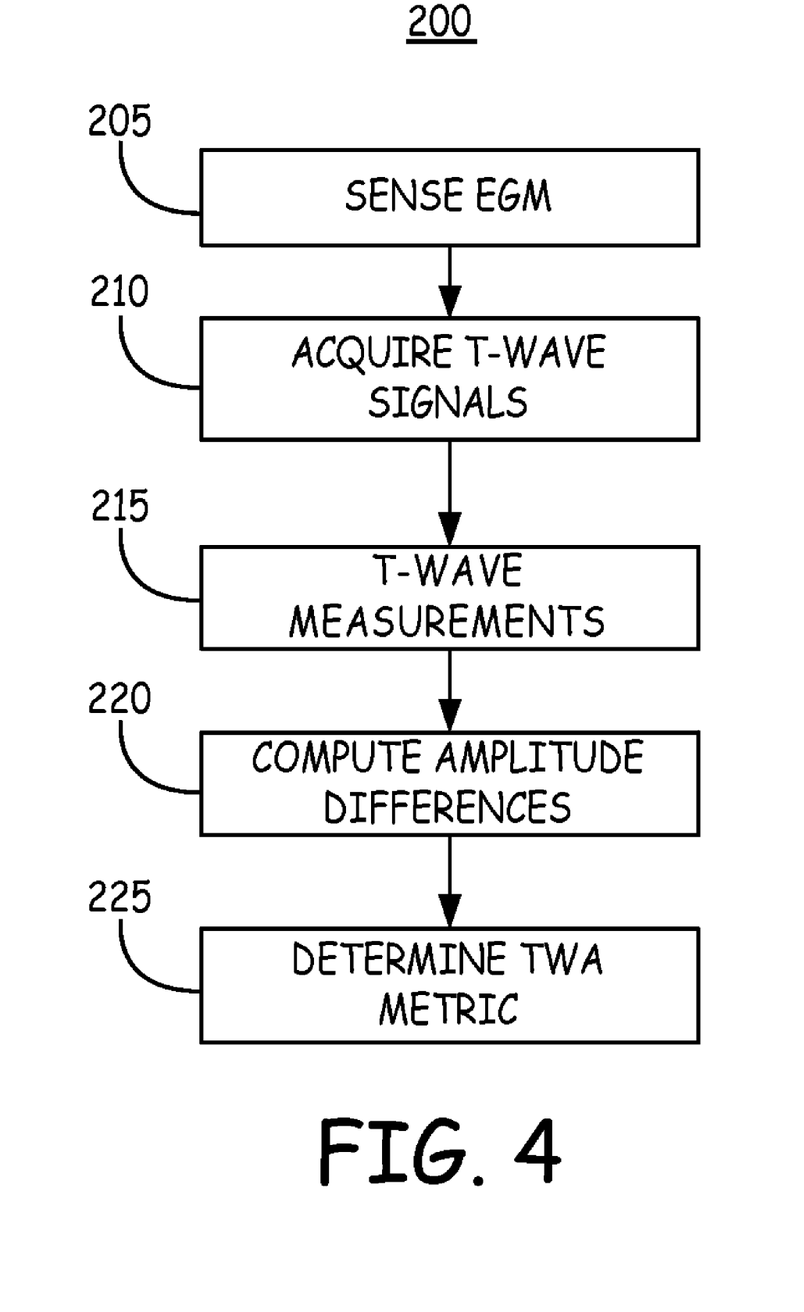
FIG. 4 is a flow chart summarizing a method for assessing TWA according to one embodiment of the invention.

FIG. 4 is a flow chart summarizing a method for assessing TWA according to one embodiment of the invention. Flow chart 200 is intended to illustrate the functional operation of an IMD system, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 for assessing TWA includes sensing an EGM signal at block 205. T-wave signals are acquired by the IMD subsequent to the sensed R-waves at block 210. Typically, a T-wave sensing window is set relative to detected R-waves for acquiring and storing a plurality of consecutive T-wave signals, for example 10 to 20 T-wave signals. The current heart rate (HR) may be recorded at block 210 for use in determining a TWA metric. Generally, if a TWA episode occurs, it will occur during an elevated heart rate. Depending on a disease state or other physiological conditions, a longer TWA episode or an episode having greater differences between alternating T-waves may occur at relatively lower heart rates. As such, the HR corresponding to a TWA episode may be used in determining a TWA metric. Methods for acquiring T-wave signals for TWA assessment are generally described in U.S. Pat. Pub. No. 2006/0116592 (Zhou, et al.), incorporated herein by reference in its entirety.

At block 215, T-wave measurements are performed using the acquired T-wave signals. T-wave measurements may include detecting any feature of the T-wave signal known to alternate during a TWA episode. Among the T-wave measurements that may be made are T-wave amplitude and T-wave area (integral). In one embodiment of the present invention, at least two amplitudes are determined from each T-wave signal. The amplitudes determined from each T-wave signal may be stored in a T-wave matrix in which T-waves are assigned an A or B label in an alternating manner as generally disclosed in U.S. Patent Publication No. 2006/0116596 (Zhou, et al.), hereby incorporated herein by reference in its entirety.

Two signal amplitudes determined for each T-wave signal may be a maximum peak and a minimum peak amplitude to enable determination of a difference in peak-to-peak amplitudes of alternating T-wave signals. Alternatively, the two or more amplitudes are determined from signal samples occurring at spaced apart intervals along the T-wave signal. In still other embodiments, amplitudes of T-wave signal sample points identified as fiducial points of the T-wave signal or at specified intervals relative to a reference time point may be determined.

At block 220, differences between corresponding sample point amplitudes in a pair of consecutive T-wave signals are computed. These differences are used at block 225 for computing a TWA metric.

As described in the previously-incorporated '592 published application, the T-wave measurements may be evaluated for possible contamination due to artifacts or signal noise. This evaluation is based on the differences between "A" and "B" T-wave measurements occurring in the T-wave signals. If TWA is present, the differences in the "A" and "B" T-wave measurements will be consistent in phase evidencing an A-B-A-B-A-B pattern. For example, if T-wave amplitudes are measured, the "A" T-wave amplitudes will be greater than the "B" T-wave amplitudes most of the time or less than the "B" T-wave amplitudes most of the time. Considerable variation in the comparative relation of the "A" and "B" T-wave measurements does not evidence an alternans pattern. As such, determination of a TWA metric may include verification that the beat-to-beat differences between "A" and "B" T-wave measurements are consistent in phase. If the differences are changing in phase, i.e., "A" measurements are sometimes greater and sometimes less than "B" measurements, the TWA measurement may not be clinically meaningful. The TWA consistency may be evaluated by determining the percentage of all beat-to-beat differences being of the same phase. The TWA assessment may further include detecting premature ventricular contractions and eliminating data corresponding to T-wave signal pairs that include a premature ventricular contraction.

Figure 5A:
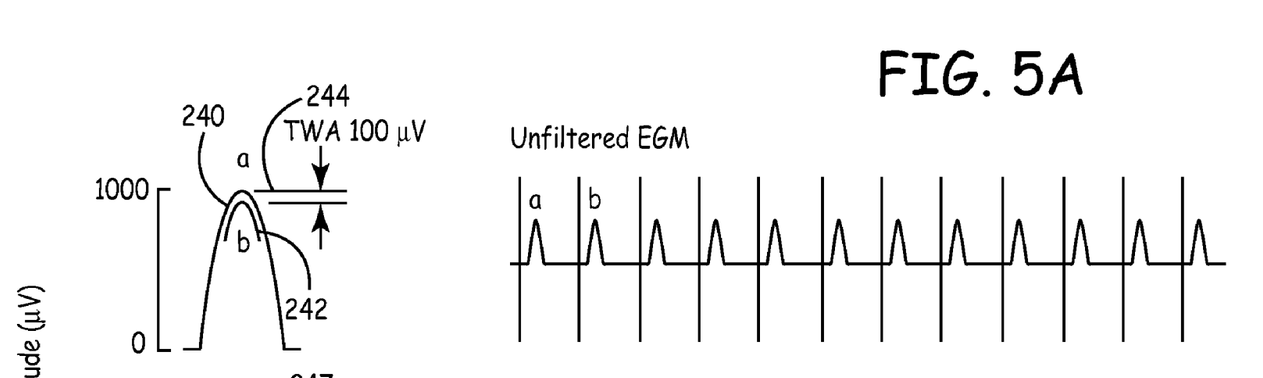
FIG. 5A is a diagram of superimposed consecutive T-wave signals illustrating the presence of TWA.

FIG. 5A is a diagram of superimposed consecutive T-wave signals illustrating the presence of TWA. The consecutive T-wave signals form a T-wave signal pair that can be evaluated for detecting TWA. The T-wave signals 240 and 242 have been obtained using minimal filtering, e.g., wide band filtering of 0.05 to 1000 Hz, as might be used in external ECG monitoring. The T-wave signals 240 and 242 are monophasic signals, and the T-wave signal "A" 240 has a greater maximum peak amplitude than the T-wave signal "B" 242. Methods used in past practice, such as the Modified Moving Average method, have relied on the maximum peak amplitude difference 244 between T-wave pairs in detecting the presence of TWA.

Figure 5B:
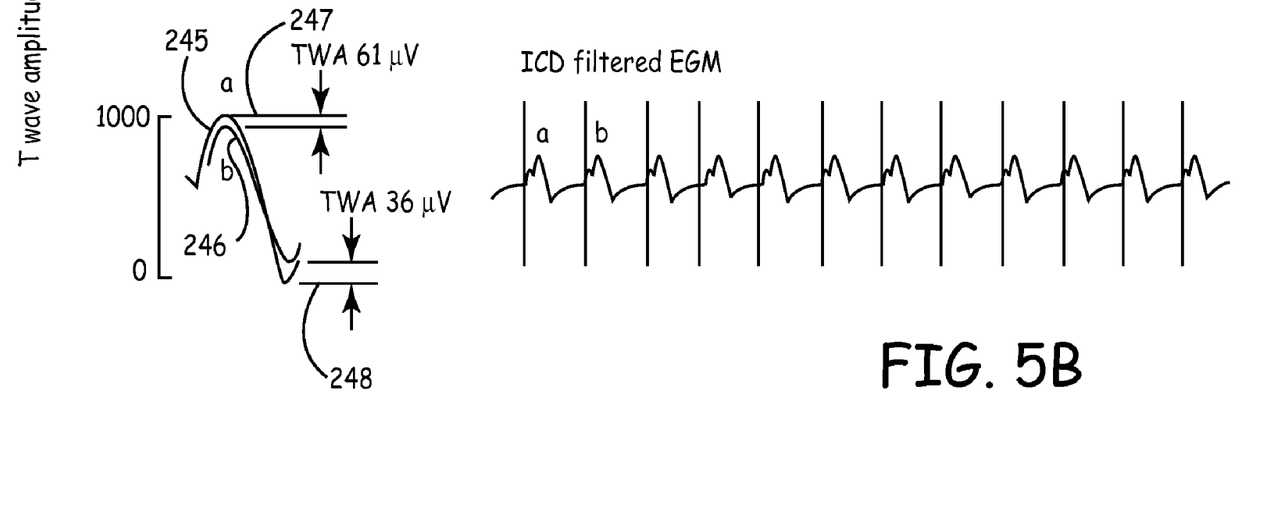
FIG. 5B is a diagram of superimposed consecutive T-wave signals acquired during TWA using narrow band filtering, e.g. 3 to 100 Hz filtering, as might be used in ICDs.

FIG. 5B is a diagram of superimposed consecutive T-wave signals acquired during TWA using narrow band filtering, e.g. 3 to 100 Hz filtering, as might be used in ICDs. The consecutive T-wave signals 245 and 246 form a T-wave signal pair that can be evaluated for detecting TWA. The T-wave signals 245 and 246 become biphasic signals after filtering by the ICD. T-wave signal "A" 245 has a greater maximum peak amplitude than the T-wave signal "B" 246, however the difference 247 is diminished relative to the peak difference 244 of the relatively unfiltered signals 240 and 242 of FIG. 5A. The magnitude of the TWA is somewhat reduced due to the ICD filtering methods and the total effect of the alternans on the T-wave signal is divided between the two phases of the filtered EGM signals 245 and 246. As such, an amplitude difference 248 is also present between the minimum peak amplitudes of the signals 245 and 246. Methods used in past practice, such as the Modified Moving Average method, which rely on the maximum peak amplitude difference 247, and do not take into account amplitude differences of a minimum peak or other T-wave signal points, will be less sensitive to detecting TWA when applied to ICD filtered T-wave signals.

Figure 6A:
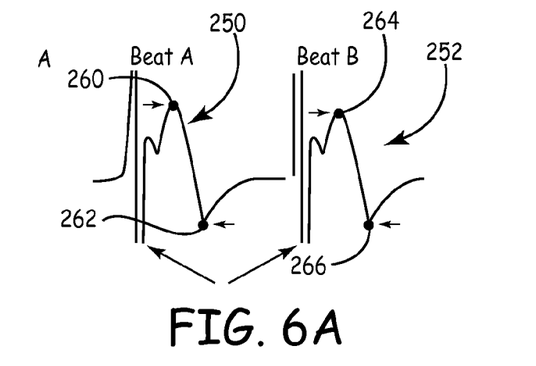
FIG. 6A is a diagram of a pair of T-wave signals illustrating one method for evaluating T-wave signal pairs for detecting TWA in an implantable device.

FIG. 6A is a diagram of a pair of T-wave signals illustrating one method for evaluating T-wave signal pairs for detecting TWA in an implantable device. The T-wave signals shown in FIG. 6A include a first T-wave labeled as an "A" T-wave signal 250 followed consecutively by a second T-wave labeled as a "B" T-wave signal 252. For each T-wave signal 250 and 252, two amplitudes are determined. For the first T-wave signal 250, a maximum peak amplitude 260 and a minimum peak amplitude 262 is determined. Likewise, for the next consecutive T-wave signal 252, the maximum peak amplitude 264 and the minimum peak amplitude 266 are determined. In one embodiment of the invention, the difference between the peak maximum amplitudes 260 and 264 and the difference between the peak minimum amplitudes 262 and 266 for the T-wave signals 250 and 252 are determined for use in computing a metric of TWA.

Figure 6B:
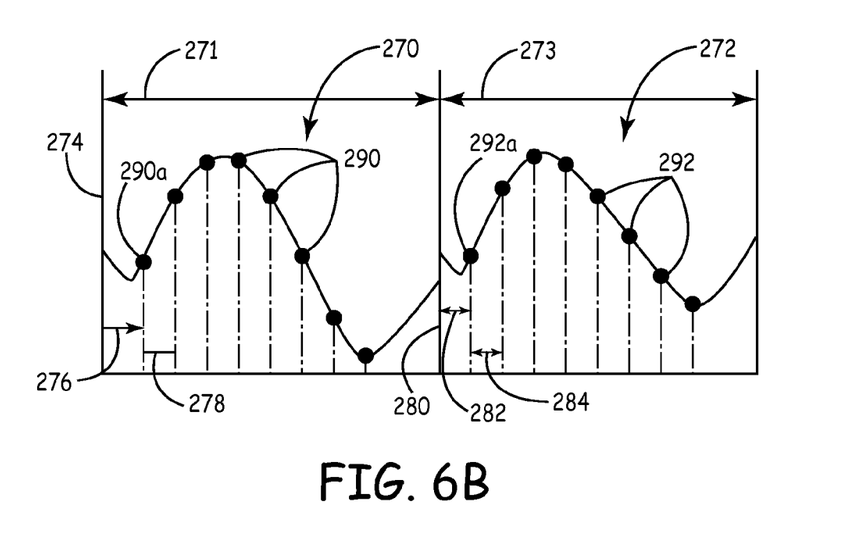
FIG. 6B is a diagram of a pair of T-wave signals illustrating an alternative method for evaluating T-wave signal pairs for detecting TWA in an implantable device.

FIG. 6B is a diagram of a pair of T-wave signals 270 and 272 illustrating an alternative method for evaluating T-wave signal pairs for detecting TWA in an implantable device. TWA can manifest during the ascending or descending phases of a T-wave signal. As such, in some embodiments, measurements of signal point amplitudes along the ascending and/or descending phases of the T-wave signal, in addition to or alternatively to detecting maximum and minimum peak amplitudes, may result in greater sensitivity to detecting TWA, especially when TWA is not occurring at the peak of T wave.

T-wave signals 270 and 272 are sensed during consecutive T-wave sensing windows 271 and 273, respectively. A number of signal amplitudes 290 and 292 are determined from each T-wave signal 270 and 272 along the ascending and descending phases of the T-wave signals 270 and 272. A first signal amplitude 290a may be determined from the first T-wave signal 270 at a predetermined interval 276 relative to the start 274 of the T-wave sensing window 271. A number of signal amplitudes 290 are determined thereafter at time intervals 278, which may be equally spaced time intervals. The number of signal amplitudes determined and the time intervals 276 and 278 used may vary between embodiments.

Likewise a first signal amplitude 292a is determined at a time interval 282 following the start 280 of sensing window 273. A number of signal amplitudes 292 are determined thereafter at time intervals 284. The difference between the amplitudes 290 and respective amplitudes 292 occurring at corresponding time intervals during the consecutive T-wave sensing windows 270 and 272 are computed for use in determining TWA metric.

Figure 7:
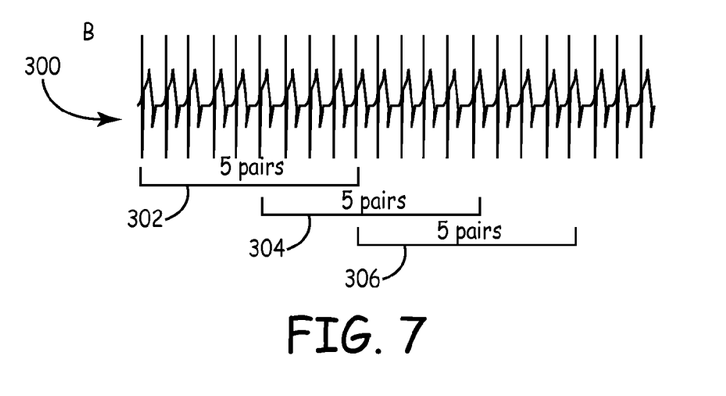
FIG. 7 is an EGM signal indicating sliding signal analysis windows encompassing a selected number of T-wave signal pairs.

FIG. 7 is an EGM signal indicating sliding signal analysis windows encompassing a selected number of T-wave signal pairs. In one embodiment of the invention, computations for determining differences between the amplitudes of selected T-wave signal sample points are performed for a predetermined number of T-wave signal pairs during a sliding analysis window. For example, a first set of five consecutive T-wave signal pairs may be obtained during the first analysis window 302 which includes 10 cardiac cycles. The analysis window 304 also includes 10 cardiac cycles from which another set of five consecutive pairs of T-wave signals may be analyzed. Analysis window 304 is shifted in time relative to analysis window 302. Analysis windows 302, 304 and 306 may be overlapping as shown in FIG. 5. Alternatively, analysis windows 302, 304 and 306 may be consecutive, non-overlapping analysis windows and may be spaced apart in time or having starting times coinciding with the end time of the preceding window. While five T-wave signal pairs are shown in each analysis window 302, 304 and 306, it is recognized that an analysis window may be set to include any number of T-wave signal pairs, for example 1 pair, 5 pairs, 10 pairs, 20 pairs or any other selected number of signal pairs. Furthermore, analysis windows 302, 304 and 306 may include the same or a different number of T-wave signal pairs.

It is recognized that the analysis windows 302, 304, and 306 may be automatically extended when premature contractions or noise is detected during T-wave signal acquisition in order to allow collection of a predetermined number of T-wave signal pairs needed for performing the TWA assessment. Alternatively, if an analysis window is thought to be corrupt due to noise or premature contractions, the analysis window may be discarded and a new analysis window may be applied to obtain new data.

Figure 8:
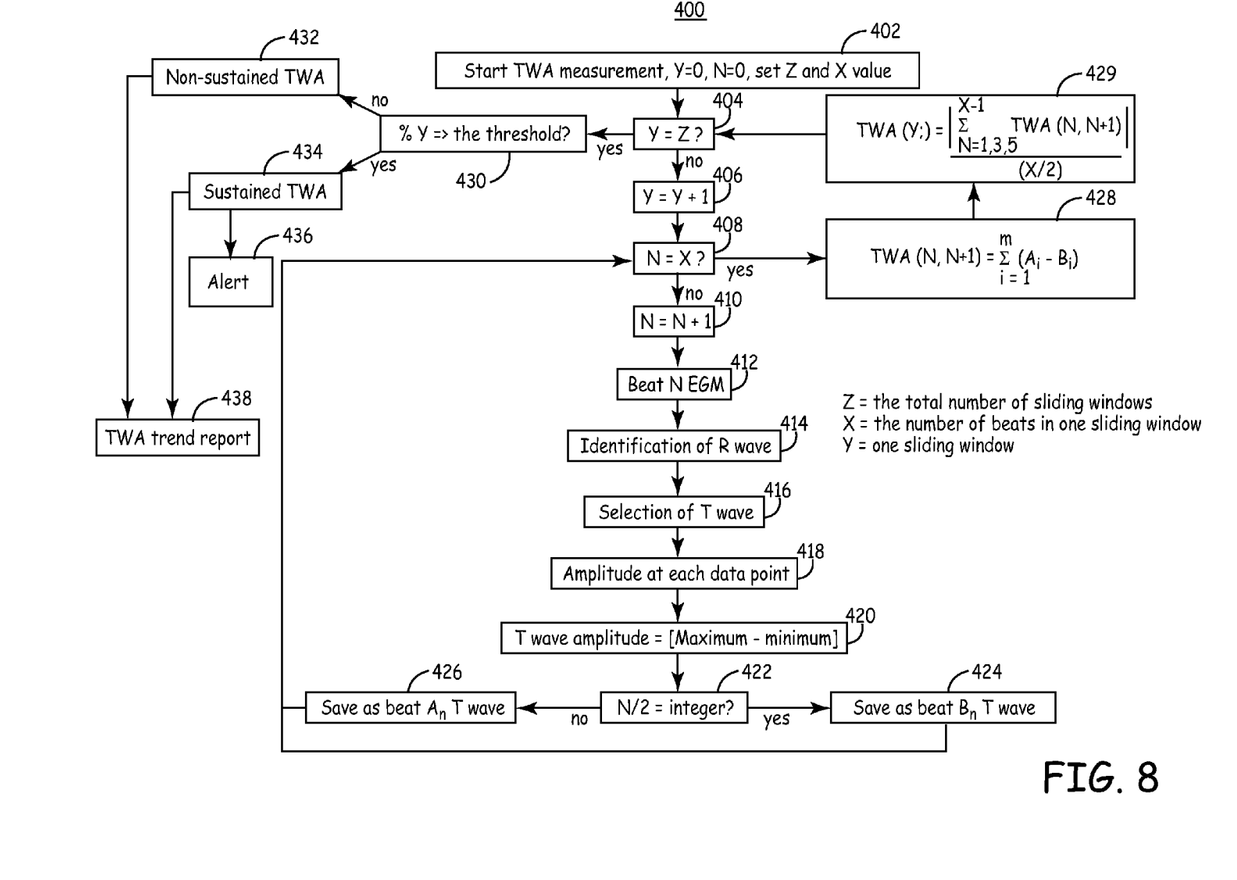
FIG. 8 is a flow chart of a method for determining a TWA metric for detecting the presence of TWA.

FIG. 8 is a flow chart of a method for determining a TWA metric for detecting the presence of TWA. At block 402, a TWA measurement is initiated. A counter Y for counting the number of analysis windows that have been applied during the assessment is initialized to zero. A counter N for counting the then number of T-wave signals to be analyzed during each analysis window is also initialized to zero. The total number of analysis windows, Z, and the total number of T-wave signals, X, to be included in each analysis window are set to desired values. For example, in one embodiment, three analysis windows each including five T-wave signal pairs (ten cardiac cycles total) may be analyzed.

At block 404, the current analysis window counter value, Y, is compared to the total number of windows to be processed Z. If the window counter Y has not reached Z, the analysis window counter Y is incremented by 1. At block 408, the T-wave signal counter N is compared to the number of T-wave signals, X, to be evaluated in each analysis window. Initially, both Y and N counters are set at zero and will be incremented at blocks 406 and 410 respectfully.

At block 412 the Nth EGM signal is acquired. The R-wave present in the EGM signal is detected at block 414 allowing the T-wave sensing window to be set to acquire the Nth T-wave signal at block 416. The T-wave signal is evaluated at block 418 to determine the amplitude of at least two signal data points. As described previously, the amplitudes of selected T-wave signal data points may include a maximum and a minimum peak data points, temporally spaced data points, or other selected data points from the T-wave signal.

In one embodiment the peak-to-peak amplitude of the T-wave is determined at block 420 using the maximum peak amplitude and minimum peak amplitude. At block 422, the Nth T-wave signal being evaluated is determined to be either an odd numbered T-wave of the X T-wave signals to be evaluated in the current analysis window or an even numbered T-wave. If the Nth T-wave signal being evaluated is an odd numbered T-wave, or "A" beat, the amplitudes of the selected data points are stored as the $A_N$ beat data at block 426. If the Nth T-wave signal being evaluated is an even numbered T-wave, or "B" beat, the amplitude data is stored as the $B_N$ beat data at block 424.

Once the amplitude data is saved for the current T-wave signal, method 400 returns to block 408 to determine if the N counter has reached the total number of T-wave signals X to be evaluated in the current analysis window. If not, blocks 410 through 426 are repeated until all beats, for example 5 to 10 beats, have been evaluated.

If the counter N equals the number of T-wave signals to be evaluated, X, as determined at block 408, the TWA metric is computed at blocks 428 and 429 for the current analysis window. In order to compute the TWA metric, amplitude differences between corresponding data points for each T-wave signal pair, including an A beat and the consecutive B beat, are summed at block 428:

$$\text{TWA}(N, N+1)_{N=1,3,5\ldots X} = \Sigma_{i=1,m}(A_i - B_i) \quad \{1\}$$

where TWA (N, N=1) is the TWA metric computed for the consecutive pairs of T-wave signals including one odd N beat, or "A" beat, and the following even N+1 beat, or "B" beat. This TWA metric for each A–B beat pair is computed by summing the differences between the amplitudes of respective $i^{th}$ data points of the A and B beats, wherein m is the total number of data point amplitudes determined for each beat. When only the maximum and minimum peak amplitudes are determined for each T-wave signal, the TWA metric for an individual beat pair is computed as the sum of the difference between the maximum peaks of the A and B beats and the difference between the minimum peaks of the A and B beats. Alternatively, the TWA metric for the individual beat pair may be computed as the difference between peak-to-peak amplitudes of the A and B beats determined at block 420.

An average TWA metric is computed at block 429 for the current analysis window by determining the average of the TWA metric computed for the X/2 individual beat pairs:

$$TWA(Y_j) = \frac{\left| \sum_{N=1,3,5\ldots X-1} (TWA(N, N+1)) \right|}{(X/2)} \quad \{2\}$$

where $TWA(Y_j)$ is the average TWA metric for the current analysis window $Y_j$ and TWA(N, N+1) are the TWA metrics computed according to Equation {1} above for T-wave signal pairs included in the current analysis window. The individual TWA metrics computed for all of the beat pairs (1 through X/2) are summed and divided by the number of T-wave signal pairs (X/2).

In an alternative embodiment, the TWA metric for the current analysis window can be computed at blocks 428 and 429 as the sum of the differences between averaged amplitudes of the respective $i^{th}$ data points as given by Equation {3}:

$$TWA(Y_j) = |\Sigma_{i=1,m}[\{(\text{sum } A_i)/(X/2)\} - \{(\text{sum } B_i)/(X/2)\}]| \quad \{3\}$$

where {sum $A_i$(X/2)} is the average of the $i^{th}$ data point amplitudes for all of the "A" beats in the analysis window $Y_j$, and {sum $B_i$/(X/2)} is the average of the $i^{th}$ data point amplitudes for all of the "B" beats in the analysis window $Y_j$. The difference between the averaged data point amplitudes of the A beats and the B beats is summed for all of the m data point amplitudes determined for a T-wave sensing window to compute the total TWA metric for the current analysis window $Y_j$. For example, when a peak maximum amplitude and a peak minimum amplitude are determined for each beat, an average peak maximum amplitude for all the A beats and an average peak maximum amplitude for all the B beats are computed. Likewise, average peak minimum amplituded for all the A beats and for the all of the B beats are computed. The difference between the average maximum peak amplitude of the A beats and the average maximum peak amplitude of the B beats is summed with the difference between the average minimum peak amplitude of the A beats and the average minimum peak amplitude of the B beats to yield $TWA(Y_j)$.

To reduce the effects of noise, which can introduce a large A–B difference, the TWA metric for a given analysis window can be computed at block 429 after rejecting the T-wave signal pair having the largest $i^{th}$ signal point amplitude difference and the T-wave signal pair having the smallest $i^{th}$ signal point amplitude difference. Alternatively, the largest and smallest TWA computed for individual beat pairs, for example according to Equation 1 above, can be rejected before computing the TWA metric for the analysis window.

After computing the average TWA metric, $TWA(Y_j)$, for the T-wave signal pairs included in the current analysis window, the window counter Y is compared to the total number of windows to be processed, Z, at block 404. If all Z analysis windows have been applied, the percentage of analysis windows resulting in an average TWA metric greater than a predetermined TWA detection threshold is determined. For example, if more than 50% of the analysis windows result in an average TWA metric greater than the TWA detection threshold, sustained TWA is detected at block 434. If less than 50% of the analysis windows result in an averaged TWA metric greater than the threshold, non-sustained TWA, or no TWA, is detected at block 432.

A response to the detection of sustained TWA may be provided at block 436, such as generating an alert signal or triggering or adjusting a patient therapy. At block 438 a TWA trend report may be updated to report the detection of sustained or non-sustained TWA. In one embodiment, a TWA burden may be tracked as the total number of analysis windows that meet the TWA detection threshold over a monitoring period, for example over 24 hours, during one night, during one week or any other selected monitoring period. A monitoring period may include continuous or intermittent bouts of TWA assessments. For example, over a one week monitoring period, TWA assessment may include 10 analysis windows applied daily on a scheduled basis or 70 analysis windows total. Alternatively or additionally, the TWA assessment may include automatically triggered TWA assessment.

The TWA burden can be an indicator of the severity of cardiac electrical instability or cardiac disease progression. The TWA burden can be expressed as an average TWA metric times the total analysis window length, resulting in units of μV×minutes. Alternatively the TWA burden may be computed as the sum of the total time interval of all the analysis windows meeting the TWA threshold criteria, resulting in units of time. The TWA burden may also be compared to a severity threshold which may trigger an alarm or other response by the device.

Figure 9A:
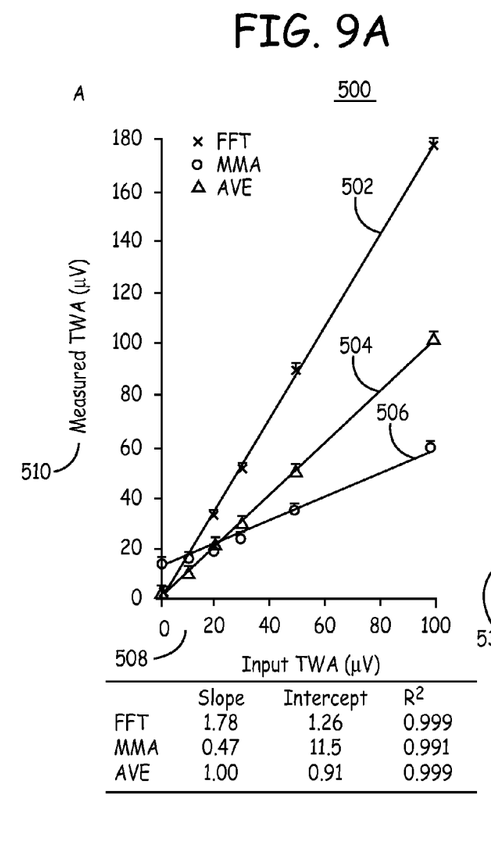
FIG. 9A is a graph of simulation results of TWA measurements performed using FFT and MMA methods compared to using a two-point amplitude assessment as described herein.

FIG. 9A is a graph 500 of simulation results of TWA measurements (y-axis 510) performed using FFT and MMA methods compared to using a two-point amplitude assessment as illustrated in FIG. 5A wherein a maximum peak and minimum peak amplitude are both compared between paired T-waves. The T-wave assessment was performed using input T-wave signals presenting TWA of magnitude 0 to 100 microvolts (x-axis 508). The input T-wave signals correspond to biphasic T-wave signals following ICD sensing circuitry processing. TWA measured 502 using the FFT method amplifies input TWA by a constant factor (slope=1.78). In the time domain, the MMA method attenuates the measured TWA 506 (slope=0.47) because the difference between the A and B beats is measured only at one peak of the biphasic T-wave resulting in an underestimate of the TWA magnitude. TWA measurements 504 made using a two-point analysis method as described herein, specifically one which computes a difference between the biphasic maximum and minimum peaks, is neither amplified nor attenuated (slope=1).

Figure 9B:
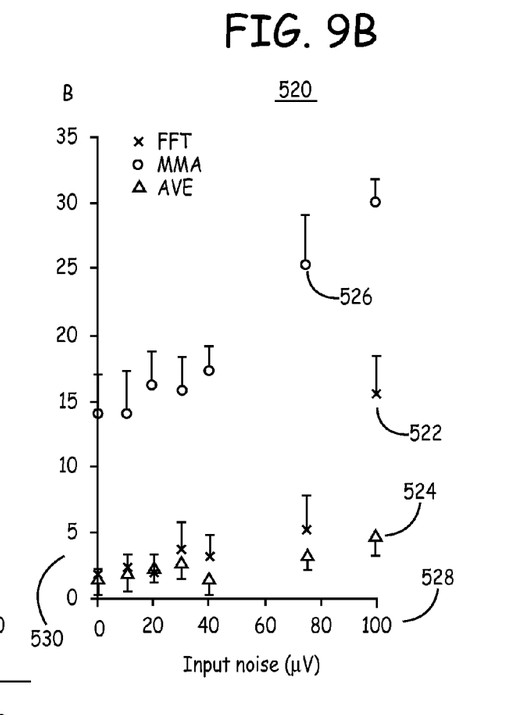
FIG. 9B is a graph of simulated TWA measurements during noise input using FFT, MMA and a two point analysis method as described herein.

FIG. 9B is a graph 520 of TWA measurements during simulated noise input 528 using FFT 522, MMA 526 and the two point analysis method 524 as described herein which compares both the maximum and minimum peaks in a biphasic T-wave signal. The MMA method 526 results in TWA measurements that are overestimated in the presence of input noise. As such, the MMA method 526 is the most sensitive to noise and the most likely to overestimate low-amplitude TWA and thus over-detect the presence of TWA.

Thus, a system and method for detecting TWA have been presented in the foregoing description with reference to specific embodiments. It is appreciated that various modifications to the referenced embodiments may be made without departing from the scope of the invention as set forth in the following claims.

The invention claimed is:

1. A method, comprising:
 sensing a cardiac electrogram (EGM) signal comprising a plurality of T-wave signals;
 selecting a pair of T-wave signals from the plurality of T-wave signals, the selected pair comprising a first T-wave signal and a second T-wave signal occurring consecutively after the first T-wave signal;
 identifying a minimum peak of each of the first and second T-wave signals;
 determining a first amplitude and a second amplitude associated with the first T-wave signal, the second amplitude being the minimum peak amplitude of the first T-wave signal;
 determining a first amplitude and a second amplitude associated with the second T-wave signal, the second amplitude associated with the second T-wave signal being the minimum peak amplitude of the second T-wave signal;
 determining a first difference between the first amplitude associated with the first T-wave signal and the first amplitude associated with the second T-wave signal;
 determining a second difference between the second amplitude associated with the first T-wave signal and the second amplitude associated with the second T-wave signal; and
 computing a T-wave alternans metric in response to the first difference and the second difference.

2. The method of claim 1 wherein the first amplitude is a maximum peak amplitude.

3. The method of claim 1 wherein the first amplitude and the second amplitude occur a predetermined time interval apart.

4. The method of claim 3 further comprising:
 determining a plurality of spaced apart amplitudes for each of the first and second T-wave signals,
 determining a plurality of differences between the plurality of spaced apart amplitudes of the first T-wave signal and the plurality of spaced apart amplitudes of the second T-wave signal; and
 computing the T-wave alternans metric using the plurality of differences.

5. The method of claim 1 further comprising:
 selecting a first plurality of pairs of T-wave signals, each pair comprising a first T-wave signal and a next T-wave signal consecutively following the first T-wave signal;
 determining a first amplitude and a second amplitude from each of the first and next T-wave signals of each of the plurality of T-wave signal pairs;
 determining a first difference between the first amplitude of the first T-wave signal and the first amplitude of the next T-wave signal for each of the plurality pair of T-wave signal pairs;
 determining a second difference between the second amplitude of the first T-wave signal and the second amplitude of the next T-wave signal for each of the plurality of T-wave signal pairs;
 computing a T-wave alternans metric using the first difference and the second difference computed for each of the plurality of T-wave signal pairs.

6. The method of claim 5 wherein computing the T-wave alternans metric comprises summing the first difference and the second difference determined for each of the plurality of T-wave signal pairs and averaging the summed first and second differences.

7. The method of claim 5 wherein determining the first difference comprises computing an average of the first amplitude for each of the first T-wave signals of the plurality of T-wave signal pairs and an average of the first amplitude for each of the second T-wave signals of the plurality of T-wave signal pairs and wherein determining the second difference comprises computing an average of the second amplitude for each of the first T-wave signals of the plurality of T-wave signal pairs and an average of the second amplitude for each of the second T-wave signals of the plurality of T-wave signal pairs.

8. The method of claim 6 further comprising selecting a next plurality of pairs of T-wave signals and computing a T-wave alternans metric for the next plurality of T-wave signal pairs.

9. The method of claim 8 wherein computing the T-wave alternans metric further comprises comparing the T-wave alternans metrics computed for the first and next plurality of T-wave signal pairs to a predetermined threshold and detecting sustained T-wave alternans in response to a predetermined percentage of the computed T-wave alternans metrics exceeding the predetermined threshold.

10. The method of claim 9 wherein computing the T-wave alternans metric further comprises computing a total time corresponding to the T-wave alternans metric exceeding the predetermined threshold.

11. An implantable medical device, comprising:
 an electrode for sensing a cardiac electrogram (EGM) signal comprising a plurality of T-wave signals;
 sensing circuitry coupled to the electrode for receiving and filtering the EGM signal;
 a processor coupled to the sensing circuitry and configured to:
  select a pair of T-wave signals from the plurality of T-wave signals, the pair of T-wave signals comprising a first T-wave signal and a second T-wave signal occurring consecutively after the first T-wave signal;
  identify a minimum peak of each of the first and second T-wave signals;
  determine a first amplitude and a second amplitude associated with the first T-wave signal, the second amplitude being the minimum peak amplitude of the first T-wave signal;
  determine a first amplitude and a second amplitude associated with the second T-wave signal, the second amplitude associated with the second T-wave signal being the minimum peak amplitude of the second T-wave signal;
  determine a first difference between the first amplitude associated the first T-wave signal and the first amplitude associated with the second T-wave signal;
  determine a second difference between the second amplitude associated with the first T-wave signal and the second amplitude associated with the second T-wave signal; and
  compute a T-wave alternans metric in response to the first difference and the second difference.

12. The device of claim 11 wherein the first amplitude is a maximum peak amplitude.

13. The device of claim 11 wherein the first amplitude and the second amplitude occur a predetermined time interval apart.

14. The device of claim 13 wherein the processor is further configured to:
- determine a plurality of spaced apart amplitudes for each of the first and second T-wave signals,
- determine a plurality of differences between the plurality of spaced apart amplitudes of the first T-wave signal and the plurality of spaced apart amplitudes of the second T-wave signal; and
- compute the T-wave alternans metric using the plurality of differences.

15. The device of claim 11 wherein the processor is further configured to:
- select a first plurality of pairs of T-wave signals, each pair comprising a first T-wave signal and a next T-wave signal consecutively following the first T-wave signal;
- determine a first amplitude and a second amplitude from each of the first and next T-wave signals of each of the plurality of T-wave signal pairs;
- determine a first difference between the first amplitude of the first T-wave signal and the first amplitude of the next T-wave signal for each of the plurality of T-wave signal pairs;
- determine a second difference between the second amplitude of the first T-wave signal and the second amplitude of the next T-wave signal for each of the plurality of T-wave signal pairs;
- compute a T-wave alternans metric using the first difference and the second difference computed for each of the plurality of T-wave signal pairs.

16. The device of claim 15 wherein computing the T-wave alternans metric comprises summing the first difference and the second difference determined for each of the plurality of T-wave signal pairs and averaging the summed first and second differences.

17. The device of claim 15 wherein determining the first difference comprises computing an average of the first amplitude for each of the first T-wave signals of the plurality of T-wave signal pairs and an average of the first amplitude for each of the second T-wave signals of the plurality of T-wave signal pairs and wherein determining the second difference comprises computing an average of the second amplitude for each of the first T-wave signals of the plurality of T-wave signal pairs and an average of the second amplitude for each of the second T-wave signals of the plurality of T-wave signal pairs.

18. The device of claim 16 further comprising selecting a next plurality of pairs of T-wave signals and computing a T-wave alternans metric for the next plurality of T-wave signal pairs.

19. The device of claim 18 wherein computing the T-wave alternans metric further comprises comparing the T-wave alternans metrics computed for the first and next plurality of T-wave signal pairs to a predetermined threshold and detecting sustained T-wave alternans in response to a predetermined percentage of the computed T-wave alternans metrics exceeding the predetermined threshold.

20. The device of claim 19 wherein computing the T-wave alternans metric further comprises computing a total time corresponding to the T-wave alternans metric exceeding the predetermined threshold.

21. A non-transitory computer-readable medium for storing a set of instructions which when implemented in an implantable medical device system cause the system to:
- sense a cardiac electrogram (EGM) signal comprising a plurality of T-wave signals;
- select a pair of T-wave signals from the plurality of T-wave signals, the selected pair comprising a first T-wave signal and a second T-wave signal occurring consecutively after the first T-wave signal;
- identify a minimum peak of each of the first and second T-wave signals;
- determine a first amplitude and a second amplitude associated with the first T-wave signal, the second amplitude being the minimum peak amplitude of the first T-wave signal;
- determine a first amplitude and a second amplitude associated with the second T-wave signal, the second amplitude associated with the second T-wave signal being the minimum peak amplitude of the second T-wave signal;
- determine a first difference between the first amplitude associated with the first T-wave signal and the first amplitude associated with the second T-wave signal;
- determine a second difference between the second amplitude associated with the first T-wave signal and the second amplitude associated with the second T-wave signal; and
- compute a T-wave alternans metric in response to the first difference and the second difference.

* * * * *